United States Patent
Vogtmeier et al.

(10) Patent No.: US 10,288,748 B2
(45) Date of Patent: May 14, 2019

(54) DOUBLE-SIDED ORGANIC PHOTODETECTOR ON FLEXIBLE SUBSTRATE

(71) Applicant: KONINKLIJKE PHILIPS N.V., Eindhoven (NL)

(72) Inventors: Gereon Vogtmeier, Aachen (DE); Roger Steadman Booker, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 501 days.

(21) Appl. No.: 15/035,515

(22) PCT Filed: Nov. 17, 2014

(86) PCT No.: PCT/EP2014/074809
§ 371 (c)(1),
(2) Date: May 10, 2016

(87) PCT Pub. No.: WO2015/071471
PCT Pub. Date: May 21, 2015

(65) Prior Publication Data
US 2016/0274249 A1 Sep. 22, 2016

(30) Foreign Application Priority Data
Nov. 15, 2013 (EP) .................. 13193104

(51) Int. Cl.
*A61B 6/00* (2006.01)
*G01T 1/20* (2006.01)
*A61B 6/03* (2006.01)
*A61B 6/04* (2006.01)

(52) U.S. Cl.
CPC ............ *G01T 1/2018* (2013.01); *A61B 6/032* (2013.01); *A61B 6/037* (2013.01); *A61B 6/0407* (2013.01); *A61B 6/4447* (2013.01)

(58) Field of Classification Search
CPC ....... G01T 1/2018; A61B 6/032; A61B 6/037; A61B 6/0407; A61B 6/4447
See application file for complete search history.

(56) References Cited

U.S. PATENT DOCUMENTS

| | | | | |
|---|---|---|---|---|
| 8,324,581 | B2 * | 12/2012 | Danzer | G01T 1/2018 250/366 |
| 8,373,132 | B2 | 2/2013 | Baeumer | |
| 9,000,382 | B2 | 4/2015 | Mattson | |
| 9,194,959 | B2 * | 11/2015 | Schmand | G01T 1/1642 |

(Continued)

FOREIGN PATENT DOCUMENTS

| | | |
|---|---|---|
| EP | 1607768 | 12/2005 |
| KR | 20120103912 | 9/2012 |

(Continued)

*Primary Examiner* — Christine S. Kim

(57) ABSTRACT

The present invention relates to a detection module (22) for the detection of ionizing radiation emitted by a radiation source (20) comprising a scintillator element (24) for emitting scintillation photons in response to incident ionizing radiation, a first photosensitive element (32*a*) optically coupled to the scintillator element (24) for capturing scintillation photons (30) and a flexible substrate (34) for supporting the first photosensitive element (32*a*). The present invention also relates to an imaging device (10) that comprises such a detection module (22).

14 Claims, 6 Drawing Sheets

(56) References Cited

U.S. PATENT DOCUMENTS

| | | | | |
|---|---|---|---|---|
| 2003/0031296 A1* | 2/2003 | Hoheisel | ............... | G01T 1/2018 |
| | | | | 378/98.8 |
| 2004/0016886 A1* | 1/2004 | Ringermacher | ...... | G01T 1/2018 |
| | | | | 250/370.11 |
| 2004/0227091 A1* | 11/2004 | LeBlanc | ............... | G01T 1/1642 |
| | | | | 250/366 |
| 2008/0011960 A1 | 1/2008 | Yorkston | | |
| 2009/0008562 A1* | 1/2009 | Grazioso | ............... | G01T 1/1644 |
| | | | | 250/363.04 |
| 2013/0168750 A1 | 7/2013 | Ikhlef | | |
| 2013/0292574 A1 | 11/2013 | Levene | | |

FOREIGN PATENT DOCUMENTS

| | | |
|---|---|---|
| WO | 2007/039840 | 4/2007 |
| WO | 2008/129433 | 10/2008 |
| WO | 2009/060349 | 5/2009 |
| WO | 2012/080927 | 6/2012 |
| WO | 2012/127403 | 9/2012 |

\* cited by examiner

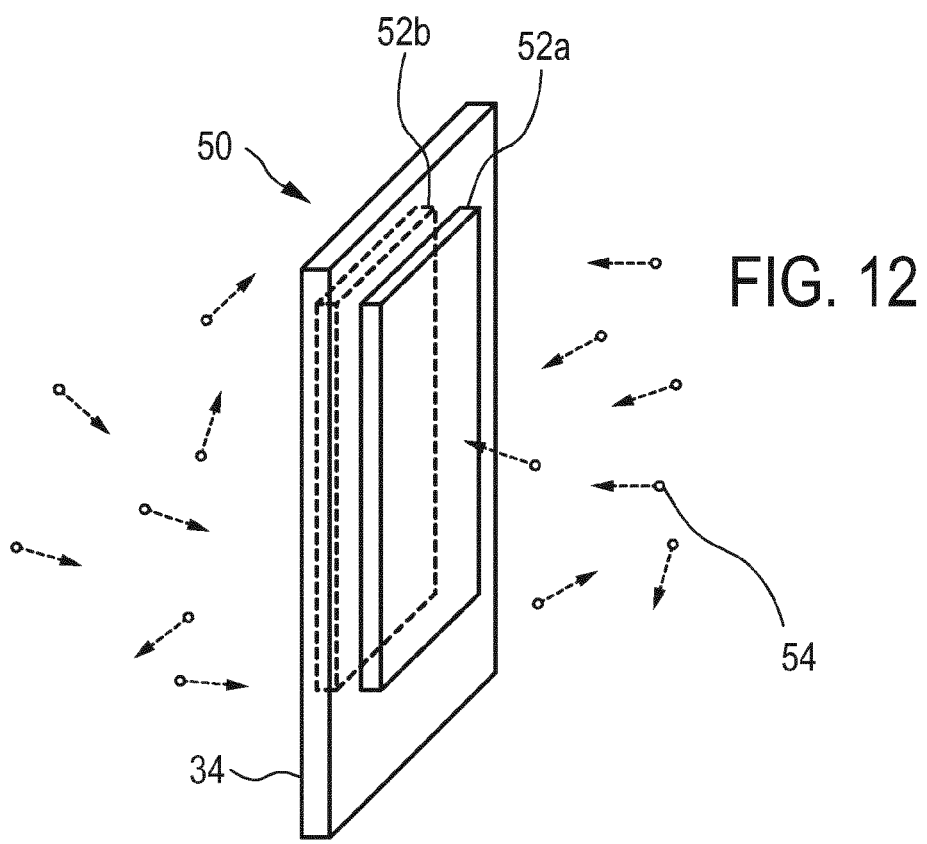

DOUBLE-SIDED ORGANIC PHOTODETECTOR ON FLEXIBLE SUBSTRATE

CROSS REFERENCE TO RELATED APPLICATIONS

This application is the U.S. National Phase application under 35 U.S.C. § 371 of International Application No. PCT/EP2014/074809, filed Nov. 11, 2014, published as WO 2015/071471 on May 21, 2015, which claims the benefit of European Patent Application Number 13193104.0 filed Nov. 15, 2013. These applications are hereby incorporated by reference herein.

FIELD OF THE INVENTION

The present invention relates to a detection module for the detection of ionizing radiation emitted by a radiation source. The present invention further relates to an imaging system for providing images of a subject.

BACKGROUND OF THE INVENTION

In medical diagnosis applications, one important issue is the generation of images of a patient based on the detection of ionizing radiation. In this context, various imaging methods and systems exist, such as computed tomography (CT), positron emission tomography (PET) and single-photon emission computed tomography (SPECT). Such imaging systems make use of detection modules that allow the generation of images based on detected radiation. A detection module therefor usually comprises a scintillation detector (sometimes also referred to as scintillator), in particular a scintillator crystal or an array of scintillator crystals, and a photosensor (sometimes also referred to as photodetector). The scintillator scintillates, i.e. emits light flashes (scintillation photons), in response to incoming ionizing radiation (i.e. impinging particles such as electrons, alpha particles, ions or high-energy photons etc.). The emitted photons are captured by the photosensor. Based on where, when and which number of scintillation photons is captured the temporal and spatial position and/or intensity of the incident ionizing radiation on the scintillation detector can be determined. It then becomes possible to generate an image of an object or imaging subject interacting with the ionizing radiation.

One technique thereby relates to generating an image corresponding to the intensity of the captured ionizing radiation. One difficulty with energy-resolved imaging is a possibly high-energy bandwidth of the incident ionizing radiation. In the context of CT imaging, the development of the double decker technology is one option to solve the problem of energy-resolved CT imaging. Other technologies are, e.g., counting detectors. Such a double decker detector may use a stack of, e.g., two scintillator crystals mounted on top of each other. The detection of the emitted scintillation light may then be accomplished by a double-photodiode (photosensor) mounted at the side of one pixel (two scintillator crystals). Each of the two photodiodes is intended to collect the light of the adjacent scintillator element.

In WO 2012/127403 A2, a method that includes obtaining a photosensor substrate having two opposing major surfaces is disclosed. One of the two opposing major surfaces includes at least one photosensor row of at least one photosensor element, and the obtained photosensor substrate has a thickness equal to or greater than one hundred microns. The method further includes optically coupling a scintillator array to the photosensor substrate. The scintillator array includes at least one complementary scintillator row of at least one complementary scintillator element, and the at least one complementary scintillator row is optically coupled to the at least one photosensor row and the at least one complementary scintillator element is optically coupled to the at least one photosensor element. The method further includes thinning the photosensor substrate optically coupled to the scintillator producing a thinned photosensor substrate that is optically coupled to the scintillator and that has a thickness on the order of less than one hundred microns.

US 2013/0292574 A1 discloses an imaging system including a radiation sensitive detector array. A scintillator array layermay be provided on a photosensor array layer including a two-dimensional array of photodiodes mounted on a substrate. It is reported that a photodiode may be mounted directly on a film, such as a plastic or polyamide sheet. Alternatively, a thin photodiode array may be printed on a flexible plastic sheet.

US 2008/0011960 A1 pertains to a radiographic imaging apparatus having two panels, each of them including a substrate, an array of signal sensing elements and readout devices, a passivation layer and a scintillating phosphor layer.

WO 2007/039840 A2 refers to an X-ray detector array having a number of detector elements. Each detector element includes a scintillator, a photodetector optically coupled to the scintillator and a circuit board. The circuit board may be a flexible circuit including a polymer substrate. One problem of such detectors is, however, that the efficiency, i.e. the light collection efficiency, may be limited due to the limited area of the photosensor being in contact with the scintillator elements. A possible compensation for this includes the application of a suitable reflecting material at the other side of the crystal, which has a disadvantage with respect to material and assembly costs. Furthermore, the area sensitive to ionizing radiation may be reduced. Still further, the optical crosstalk (i.e. detecting scintillation photons emitted by one scintillator element with another photosensitive element than intended for the readout of this scintillator element) resulting from optically coupling the photosensor to the vertical scintillator stack and also the packaging and connection of the photosensor to the tile substrate may result in a more expensive advanced packaging process.

SUMMARY OF THE INVENTION

It is an object of the present invention to provide an improved detection module for the detection of electromagnetic radiation emitted by a radiation source, in particular with regard to cost efficient assembly, better packaging and reproducibility. It is further an object of the present invention to provide a corresponding imaging system.

In a first aspect of the present invention a detection module for the detection of ionizing radiation emitted by a radiation source is presented. Said detection module comprises a scintillator element for emitting scintillation photons in response to incident ionizing radiation, a first photosensitive element optically coupled to the scintillator element for capturing scintillation photons and a flexible substrate for supporting the first photosensitive element. The flexible substrate is folded around the scintillator element to cover at least two surfaces of the scintillator element.

In a second aspect of the present invention, an imaging device is presented. Said imaging device comprises a subject support for supporting a subject in an examination area, a radiation source for emitting ionizing radiation arranged on a first side of the examination area or within the subject in the examination area, a detection module as described above arranged on a second side of the examination area for the detection of ionizing radiation emitted by the radiation source and an imaging unit for providing images based on the spatial distribution of the detected ionizing radiation.

Preferred embodiments of the invention are defined in the dependent claims. It shall be understood that the claimed imaging device has similar and/or identical preferred embodiments as the claimed detection module and as defined in the dependent claims.

The present invention is of particular importance in medical or other imaging applications. In such imaging applications some sort of radiation source emits ionizing radiation, i.e. radiation that includes particles with an individual kinetic energy high enough to liberate an electron from an atom or a molecule and thereby ionizing it. Particularly, ionizing radiation in the context of imaging refers to gamma rays or UV-rays. A radiation source emitting this radiation may particularly refer to an X-ray tube or a particle accelerator as used in CT or X-ray imaging. A radiation source may, however, also refer to a radioactive tracer substance emitting particles because of a radial active decay process as, e.g., used in PET or SPECT imaging. This emitted ionizing radiation is captured with a scintillator element, which emits scintillation photons in response thereto. A scintillator element thereby refers to a scintillator crystal emitting light in response to incident (ionizing) radiation. In the context of the present invention the scintillator element may, e.g., include an inorganic crystal such as GOS, CWO, LYSO, BGO, YAG, etc.

The light emitted by the scintillator element, i.e. the scintillation photons, is captured by a photosensitive element, which is optically coupled to the scintillator element. Such a photosensitive element can be used to indicate whether the scintillator element to which said photosensitive element is coupled has been subject to incident ionizing radiation. Usually, the photosensitive element is read out by means of dedicated readout electronics, and the amount of light, i.e. the number of scintillation photons that has been captured, is determined (photon counting or charge integration). Based thereupon it then becomes possible to reconstruct the distribution of the incident ionizing radiation and to reconstruct an image.

According to the present invention, there is further included a flexible substrate for supporting the photosensitive element. As used herein, a flexible substrate particularly refers to a flex circuit or a flex foil in contrast to a rigid substrate such as a conventional printed circuit boards (PCB). Thus, a flexible substrate refers to a bendable or twistable material allowing the integration of electronic connections, components or devices. Even if electronic components originally intended for the use with conventional PCB are used at least some flexibility can be preserved. A flexible substrate particularly refers to a flexible organic or plastic substrate such as polyimide (PI), polyether ether ketone (PEEK), etc.

In comparison to conventional detection modules, the detection module according to the present invention has the advantage that the flexible substrate allows a more efficient assembly process. The connection (mechanical and electrical connection) of such a flexible substrate and the thereby supported photosensitive elements to readout electronics can be simplified because it is possible to easily bring the substrate into a suitable mounting position, in particular by bending it. Thereby, the costs of the expensive mounting process and/or the packaging of the detection module can be considerably reduced. Further, the use of a flexible, in particular organic, substrate may lead to a higher packaging density.

Still further, a flexible substrate and the thereby supported electronic components can be connected (i.e. brought in contact) with other components (e.g. the scintillator elements), which are also in bent condition (e.g. bent around a corner or connected to a non-flat surface).

In a preferred embodiment the detection module further comprises a second photosensitive element for capturing scintillation photons, wherein the flexible substrate is substantially planar and the first photosensitive element is located on a first surface of the substantially planar flexible substrate and the second photosensitive element is located on a second surface of the substantially planar flexible substrate opposite the first surface. According to this embodiment, the flexible substrate supports two photosensitive elements on each of its two surfaces. Thereby, the first photosensitive element is still coupled to the scintillator element and captures the scintillation photons emitted in this scintillator element. The second photosensitive element on the opposite surface of the flexible substrate may then, e.g., be coupled to another scintillator element being arranged next to the first scintillator element with the flexible substrate and the two photosensitive elements in between. Thereby, the collection of light, i.e. scintillation photons, from scintillator elements on both sides of the flexible substrate becomes possible. Thus, two scintillator elements can be read out by means of a common mechanical support structure. Both photosensitive elements can be read out individually. Further, such a detection module with photosensitive elements on both sides (double-sided module) could also be advantageous in applications, in which light from both sides is to be collected at the same time, e.g. for a balancing sensor for measuring the amount of light on one side versus the amount of light from the other side.

According to another embodiment, the first and/or the second photosensitive element is substantially made of an organic material, in particular a polymer. Organic electronics particularly use electrically conductive polymers instead of inorganic conductors. Such conductive polymers are usually lighter and provide flexibility. The photosensitive elements may particularly be represented by organic photodiodes. Such an organic diode usually consists of a film or layer of an organic compound deposited on the flexible substrate. One particular advantage of using an organic material for the photosensitive elements is that a very thin and flexible construction can be obtained. "Substantially" as used in the present application may particularly refer to a high percentage (in this context a high percentage of organic material in comparison to inorganic support structures) such as at least 90%, preferably 95%, or more preferably more than 99%. Using an organic photodiode in combination with a flexible substrate allows a flexible, bendable photo detection assembly. This may result in the advantage that it becomes possible to cover a scintillator element not only planar but also, e.g., from different sides by bending it around a corner or edge.

Preferably, the flexible substrate is substantially made of an organic material, in particular a polymer. Using a polymer for the flexible substrate allows easily and efficiently manufacturing a substrate in the desired geometry. Thereby different geometries are possible.

In yet another embodiment of the detection module, the flexible substrate includes an intransparent layer or is substantially made of an intransparent material for preventing scintillation photons from passing through the flexible substrate. If the flexible substrate is intransparent, the optical crosstalk, i.e. the detection of scintillation photons emitted by another scintillator element than the scintillator element that the photosensitive element is coupled to, is reduced or even completely prevented. Thereby, it is either possible that an (optically) intransparent layer is included in the flexible substrate or that the whole substrate is (substantially) made from an intransparent material. In known solutions a comparably high amount of optical crosstalk was often compensated by including a reflecting material at one or more surfaces of the scintillator element potentially resulting in higher costs and a more complex manufacturing or assembly process. In contrast thereto, the present invention may allow reducing costs by not requiring such a reflecting material. Furthermore, the efficiency may be increased as the sensitive area of the detector module may be increased. Preventing scintillation photons from passing through the flexible substrate allows independently operating two photosensitive elements on both surfaces of the substrate. Scintillation photons emitted by a scintillator element coupled to the first photosensitive element are not captured by a second photosensitive element located on another side of the flexible substrate.

In yet another embodiment, the first and/or the second photosensitive element is printed on the flexible substrate. One advantage of using organic electronics is that it is possible to use printing methods for manufacturing electrical devices on various substrates. Thereby, thin film electronics can be printed, e.g. by means of electrically functional electronic or optical ink. Such inks are usually based on carbon, often in combination with silver or other conductive materials for printing conductive lines. It may thereby be possible to print one or more photosensitive elements on one or more sides or surfaces of the flexible substrate. Thereby, various geometries and arrangements of the photosensitive elements are possible. It is further possible to use a two-side printing process wherein photosensitive elements are printed on both surfaces of a flexible substrate. This printing process may be sequential, i.e. print on one side after the other, or parallel, i.e. print on both sides at the same time. It is also possible to print the required connection circuitry. Another advantage is that printing may allow reducing manufacturing costs.

In a preferred embodiment, the flexible substrate includes a first support layer for supporting the first photosensitive element and a second support layer for supporting the second photosensitive element, and the first and the second support layers are attached to one another by means of glue, in particular by means of optically isolating glue forming an intransparent layer in between the first and the second support layer. In contrast to printing the photosensitive elements on two sides or surfaces of a flexible substrate, it is also possible to make use of a substrate comprising two layers wherein each of the layers supports one photosensitive element. It is thereby not necessary to use a two-side manufacturing process, i.e. a process allowing attaching or printing a photosensitive element on both sides (surfaces) of a flexible substrate. If the substrate includes two layers, these two layers may be attached to one another by means of glue, wherein usually the two layers are substantially planar, have a photosensitive element on one surface and are glued to one another with the surface that has no photosensitive element on it. It is thereby particularly advantageous to make use of optically intransparent glue that forms an intransparent layer and prevents scintillation photons emitted on one side of the flexible substrate from passing to the other side of the flexible substrate through the different layers (optical crosstalk). One advantage of manufacturing the flexible substrate from different layers (i.e. in particular two or more layers) is that manufacturing costs may be reduced. Further, it may be possible to gain a greater flexibility with respect to geometrical forms and the arrangement of one or more photosensitive elements on the flexible substrate.

In another embodiment of the detection module, the scintillator element is substantially cuboid-shaped with a first surface facing the radiation source and the flexible substrate is arranged parallel to a second surface of the scintillator element, said second surface being arranged orthogonal to said first surface. According to this embodiment, the flexible substrate is arranged parallel to the scintillator element. Thus, the incident radiation usually impinges on one surface of the cuboid-shaped scintillator element and causes the emission of scintillation photons in the scintillator element. These scintillation photons are detected by means of a photosensitive element coupled to a side surface, i.e. to a surface orthogonal to the direction of the radiation source. It may also be possible to use a reflective material on one or more of the remaining surfaces of the cuboid-shaped scintillator element. One advantage of this arrangement again lies in the possibility of efficient manufacturing. It becomes possible to use one flexible substrate with a photosensitive element attached to one surface for capturing the scintillation photons emitted by a first scintillator element and attaching a second photosensitive element to the second surface of the flexible substrate and capturing therewith the scintillation photons emitted by a scintillator element on the other side of the flexible substrate.

In yet another embodiment, the detection module as described above further comprises a readout electronics for providing information on the spatial distribution of the incident ionizing radiation, wherein the flexible substrate includes a connection circuitry for connecting photosensitive elements to the readout electronics. Usually, a readout electronics is connected to the photosensitive elements and allows providing information, i.e. a readout, representing the spatial distribution of the captured radiation or the emitted scintillation photons, respectively. Such readout electronics may particularly comprise an analog-digital-converter for determining a digital representation of the captured scintillation photons. The readout electronics may preferably be arranged on the opposite side of the radiation source for not preventing radiation from impinging onto the scintillator element and for preventing direct detection on the readout electronics. The photosensitive elements supported by the flexible substrate are usually connected thereto by means of a connection circuitry integrated in the flexible substrate. Such connection circuitry may particularly be completely or partly made of an organic material and/or may be printed on the flexible substrate. However, it may also be possible that conventional connection circuitry includes conventional devices.

The flexible substrate is folded around the scintillator element to cover at least two surfaces of the scintillator element. Due to its flexibility, the substrate allows to be folded around the scintillator element, in particular a cuboid-shaped scintillator element, and cover two (or more) surfaces of the scintillator element. Folding (i.e. wrapping or bending) the flexible substrate around a corner of the scintillator element, could even allow complete 360° coverage. It may also be possible to use two L-shaped foils covering all four surfaces of a substantially cuboid-shaped scintillator element (the side/surface facing the radiation source and the side/face facing the readout electronics are usually not covered). Thereby, the photosensitive area can be increased, i.e. the sensitivity of the detection module can be increased.

In another preferred embodiment, the detection module further comprises a second scintillator element, wherein the first and the second scintillator elements are arranged in a stack, one scintillator element being located in between the radiation source and the other scintillator element, and wherein the flexible substrate is arranged in parallel to one side surface of the stack. Such a double-decker stack of scintillator elements may particularly be advantageous in the field of energy-resolved CT imaging. Thereby, the Compton and photo-electric components of the interaction with matter can be discriminated, i.e. more information on the energy dependent attenuation properties of tissues can be gained and/or a larger bandwidth of radiation energies can be covered. Usually, the detection of scintillation photons is achieved by means of a double-photodiode mounted at the side of a stack of two scintillator elements. Each of the two photodiodes collects the light of the adjacent scintillator element. Thus, the flexible substrate arranged in parallel to one side surface of the stack usually supports two photosensitive elements facing the two scintillator elements of the stack (and possibly further photosensitive elements on its other side/surface). It may also be possible that the stack of scintillator elements comprises an optical connection layer in between the two scintillator elements, in particular a layer of light-conducting glue.

In a further embodiment, the detection module further comprises a second scintillator element, wherein the flexible substrate is arranged in between the first and the second scintillator element and the first photosensitive element is optically coupled to the first scintillator element and the second photosensitive element is optically coupled to the second scintillator element. By arranging the flexible substrate in between the first and the second scintillator element with photosensitive elements on both sides of the flexible substrate, it becomes possible to efficiently read out two adjacent scintillator elements by making use of one single substrate. This may allow reducing manufacturing costs, increasing the collection efficiency, achieving a higher packaging density and/or minimizing the required connection circuitry.

In another embodiment, the detection module further comprises a second, a third and a fourth scintillator element, wherein the first and the third scintillator elements are arranged in a first stack and the second and the fourth scintillator element are arranged in a second stack, one scintillator element in a stack being located in between the radiation source and the other scintillator element in the stack and the flexible substrate is arranged in between the first and the second stack parallel to side surfaces of the first and the second stack. Two adjacent stacks are read out by means of photosensitive elements located on the two surfaces/sides of a flexible substrate in between the two stacks. This has the advantage that, on the one hand, each scintillator element can be read out individually and, on the other hand, an efficient manufacturing process can be applied.

In yet another embodiment, the detection module further comprises a third and a fourth photosensitive element, wherein each of the first, second, third and fourth photosensitive elements is optically coupled to the corresponding first, second, third or fourth scintillator element, the third scintillator element is located on the first surface of the substantially planar flexible substrate and the fourth photosensitive element is located on the second surface of the substantially planar flexible substrate. Again, each scintillator element is read out individually.

In another aspect of the present invention a detection module is presented that comprises a first and a second photosensitive element for capturing photons; a flexible substrate for supporting the first photosensitive element on a first surface and the second photosensitive element on a second surface; wherein the flexible substrate, the first photosensitive element and the second photosensitive element are substantially made of an organic material. The flexible substrate is folded around the scintillator element to cover at least two surfaces of the scintillator element.

By using organic materials and manufacturing processes it becomes possible to design two-sided detection modules for the use in further applications. On the one hand, the photosensitive elements may be printed on both sides of the flexible substrate. On the other hand, two layers, each with a printed photosensitive element may be glued together. Further, different geometries, materials, structures, performance parameters and/or sizes of the photosensitive elements (pixels sizes) on the two sides of the flexible substrate are possible. This detection module may also be designed and varied in the same ways as explained above with regard to the different embodiments of the invention. In comparison to previous detection modules such a module may be able provide a variety of different possible properties at comparably low costs. A high flexibility is made possible. Applications of such a module may include optical measurement devices for light sensing of different spectra (wherein the flexible substrate is basically transparent) or comparative measurements (with a basically intransparent substrate) wherein the incident radiation (photons) from two sides need to be distinguished. Still further, applications in the field of measurements, sensors, photography and light detection are possible. Possible embodiments include a double-sided sensor (module) including organic material, a double-sided stacked or printed sensor (module) and a double-sided printed sensor (module).

BRIEF DESCRIPTION OF THE DRAWINGS

These and other aspects of the invention will be apparent from and elucidated with reference to the embodiment(s) described hereinafter. In the following drawings

FIG. 12 schematically illustrates a detection module according to another aspect of the present invention.

DETAILED DESCRIPTION OF THE INVENTION

Figure 1:
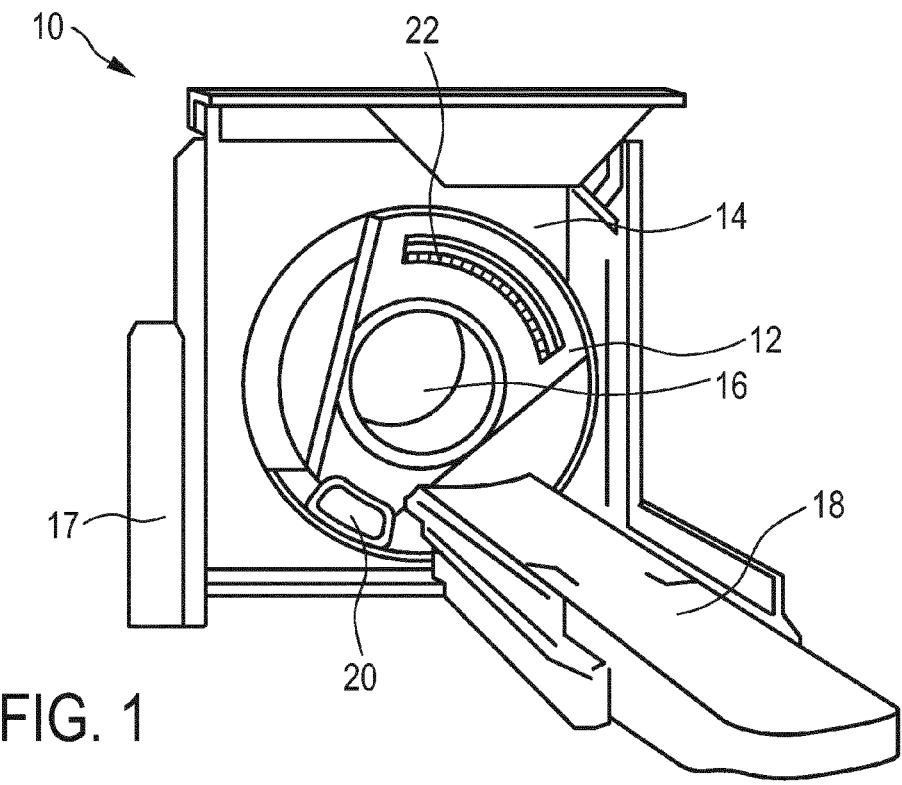
FIG. 1 shows a schematic illustration of a medical imaging device in which a detection module according to the present invention can be applied.

FIG. 1 shows the general layout of an embodiment of a medical imaging device 10, in particular a computed tomography (CT) scanner. Such a CT scanner usually includes a rotating gantry 12, which is mounted to a generally stationary gantry 14. The rotating gantry 12 is arranged to rotate around an examination area 16. It is possible to insert a subject on a subject support 18 into said examination area 16. A radiation source 20 generates ionizing radiation. This radiation passes through the examination area 16 and is detected by a plurality of detection modules 22 mounted to the rotatable gantry 12 on the other side of the examination area 16. If a subject is inserted into the examination area 16, it is possible to generate images of the subject based on an evaluation of the detected radiation. The generation and provision of images is usually carried out by means of an imaging unit 17 that may be included and/or implemented in a processing device, such as a processor or computer.

FIG. 1 illustrates one exemplary application area of the present invention. The present invention may, however, also be used with other imaging modalities such as PET or SPECT imaging, in which the radiation source is represented by a radioactive tracer substance inserted in the subject to be examined. It may also be possible to make use of the present invention in the field of traditional X-ray imaging.

Figure 2:
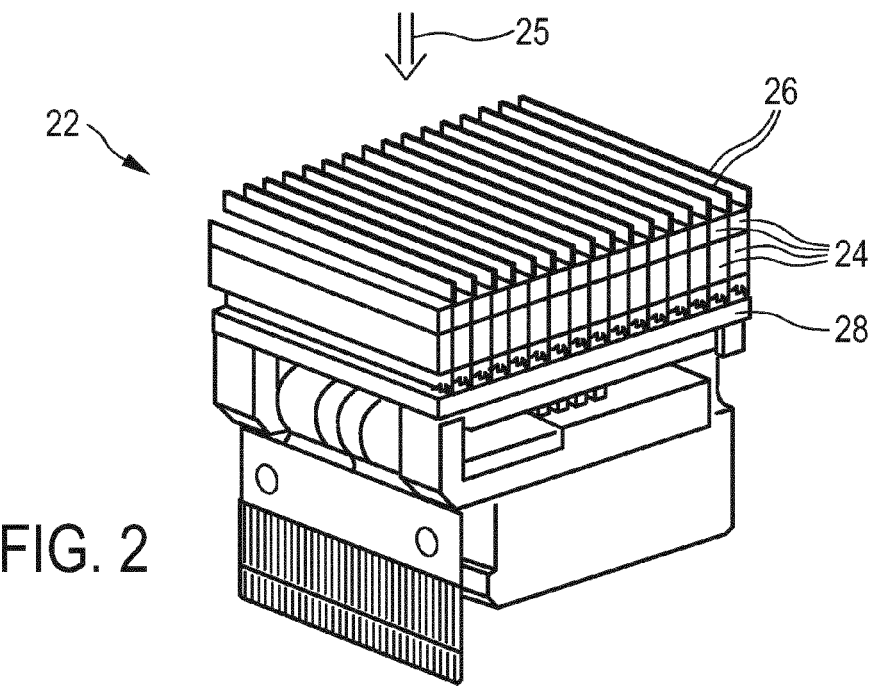
FIG. 2 shows a schematic illustration of a state of the art double decker detection module.

FIG. 2 further illustrates the general structure of an embodiment of a (state of the art) detection module 22 as e.g. used in a medical imaging device 10. Such a detection module 22 usually comprises a plurality of scintillator elements 24 emitting scintillation photons in response to incident ionizing radiation. The arrow 25 indicates the direction of the incident ionizing radiation. The module 22 further comprises photosensitive elements (not shown in FIG. 2) supported by suitable support structures 26. The photosensitive elements detect the scintillation photons and are usually connected to a readout electronics 28 for determining the layer that is hit by the incident ionizing radiation. The layer corresponds to the photon energy and is detected based on the probability of interaction of photons with one of the layers (low energy photos are likely to interact on the top layer, high energy photons are likely to interact with a lower layer). The photosensitive elements can be read out by means of photon counting or charge integration. Based on these readings, an image can be generated. The illustrated detection module is often referred to as double decker detection module as the scintillator elements 24 are arranged in stacks of two scintillator elements (in a direction of incident radiation).

Figure 3:
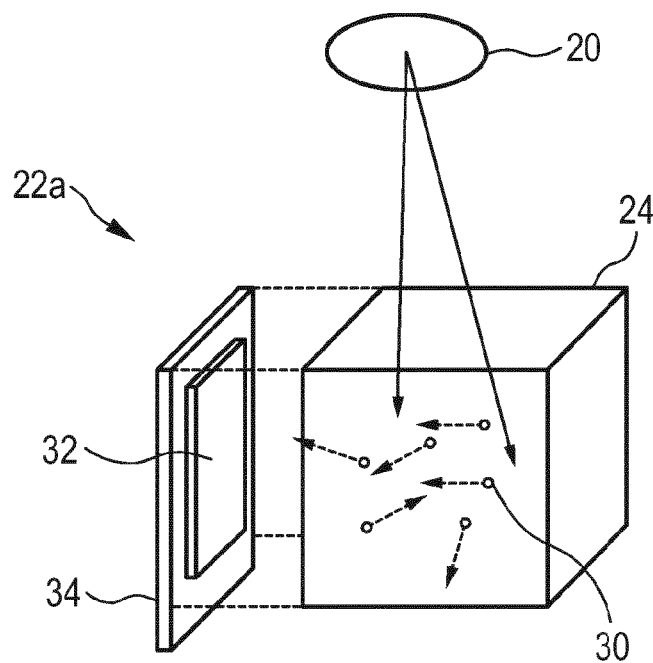
FIG. 3 shows a schematic illustration of a first embodiment of a detection module according to the present invention.

FIG. 3 illustrates a first embodiment 22a of a detection module according to the present invention, which may also be used in an imaging device 10 showing in FIG. 1. Radiation emitted by a radiation source 20 causes the emission of scintillation photons 30 in the scintillator element 24. A first photosensitive element 32 is optically coupled to the scintillator element 24 and captures the emitted scintillation photons 30. The photosensitive element 32 is supported by a flexible substrate 34 (sometimes also referred to as flex foil or, in combination with photosensitive elements coupled to it, as flex array). This flexible substrate 34 is usually substantially planar and arranged on a side surface of the scintillator element 24 orthogonal to the surface facing the radiation source 20. For better illustration, FIG. 3 shows a gap between the scintillator element 24 and the flexible substrate 34 or the first photosensitive element 32, respectively. It is to be understood that the first photosensitive element 32 is in contact, i.e. optically coupled, to the scintillator element 24. According to the present invention a flexible substrate 34 is used for supporting the photosensitive element 32. In particular, it is possible to use an organic material for supporting photosensitive elements substantially consisting of an organic material. This use of organic electronics or plastic electronics allows a cheap and efficient manufacturing and/or assembly process. The photosensitive element 32 can be printed on the substrate 34, e.g. with conductive ink. Another advantage of the present invention may result from a facilitated manufacturing/assembly of larger flexible support structures and thereby supported photosensitive elements, e.g. 128 to 256 double pixels per step. Preferably, if only one photosensitive element 32 is placed on one side of a scintillator element 24, the other sides will have a reflector (i.e. a reflective layer) attached to them due to the scattering of the scintillation photons 30. Only when all sides of the scintillator element 24 are covered by photosensitive elements 32 no reflective layers are required.

Figure 4:
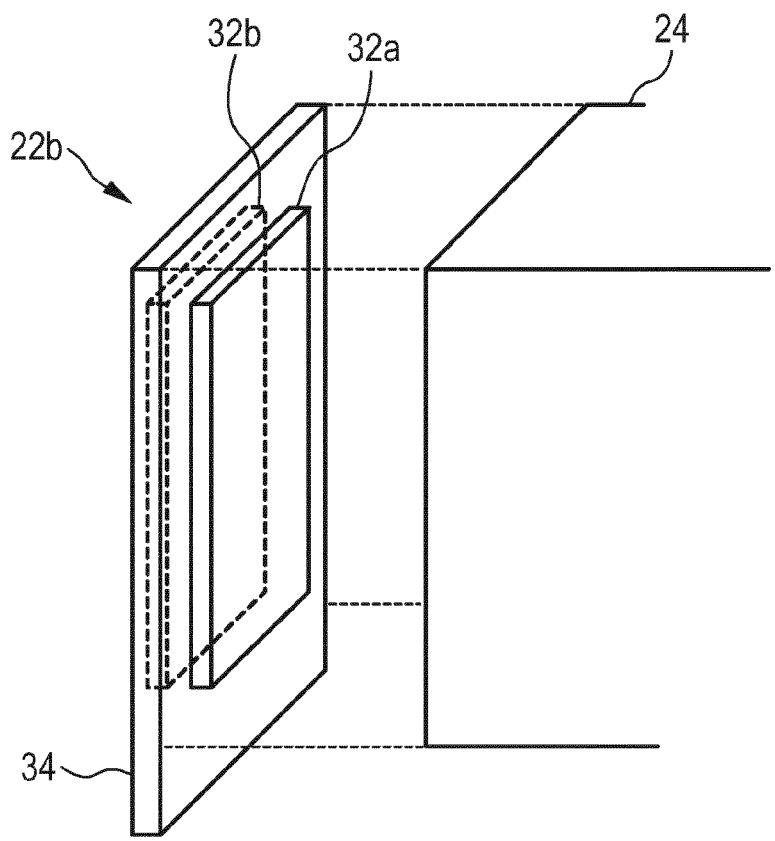
FIG. 4 shows a schematic illustration of a second embodiment of a detection module according to the present invention.

FIG. 4 illustrates a second embodiment 22b of a detection module according to the present invention. Therein, the flexible substrate 34 also supports a second photosensitive element 32b in addition to the first photosensitive element 32a. Thereby it is possible that a two-sided manufacturing process is applied. In particular, a two-sided printing process can be applied and organic photodiodes can be printed on both sides of the (organic) flexible substrate.

Figure 5:
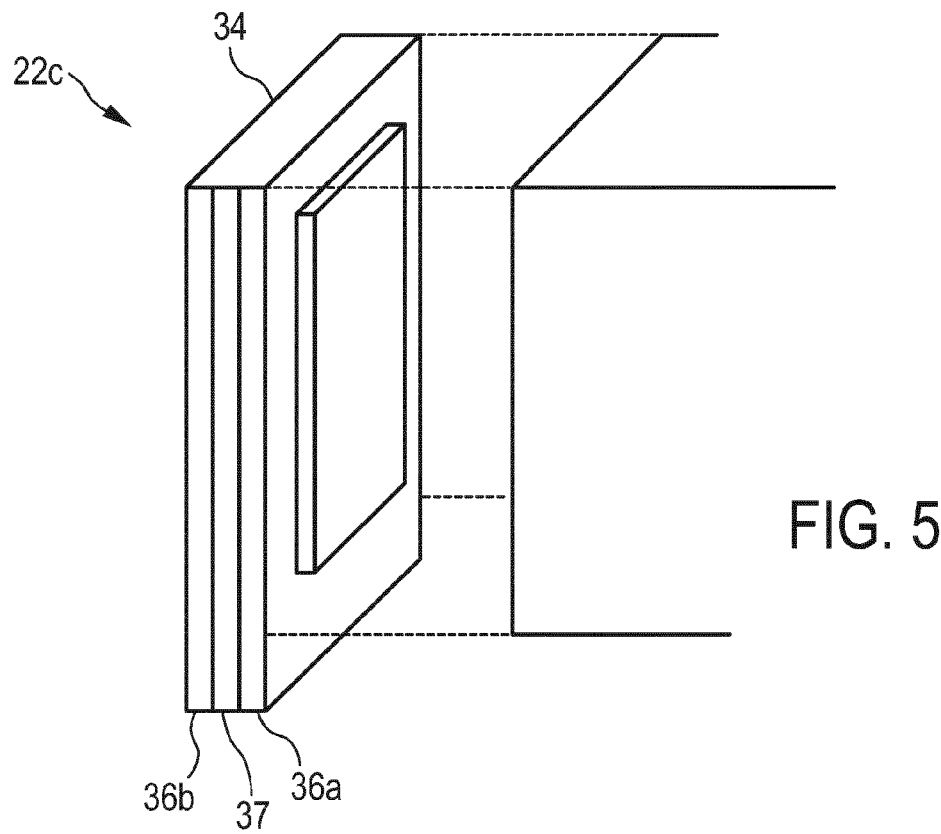
FIG. 5 shows a schematic illustration of a third embodiment of a detection module according to the present invention.

FIG. 5 shows yet another embodiment 22c of a detection module. Therein, the flexible substrate 34 includes multiple layers. The production of a flexible substrate 34 with photosensitive elements on both sides could be achieved by gluing two single-sided photodiode-flex arrays, i.e. a first 36a and a second 36b support layer, together. Thereby, the glue may form an intransparent layer 37 that prevents the scintillation photons from passing through the flexible substrate 34, and may help to reduce optical crosstalk. Depending on the manufacturing process, it may be more efficient to either use a printing process for printing a photodiode on both sides of the flexible substrate (including one single layer) or to use a one-sided printing process for printing a photodiode on a substrate (forming a support layer) and then gluing together two such substrates each with a photosensitive element (photodiode) printed on one side. Also other layer structures may be used including the use of additional layers, e.g. for electric connection or for mechanical support.

Figure 6:
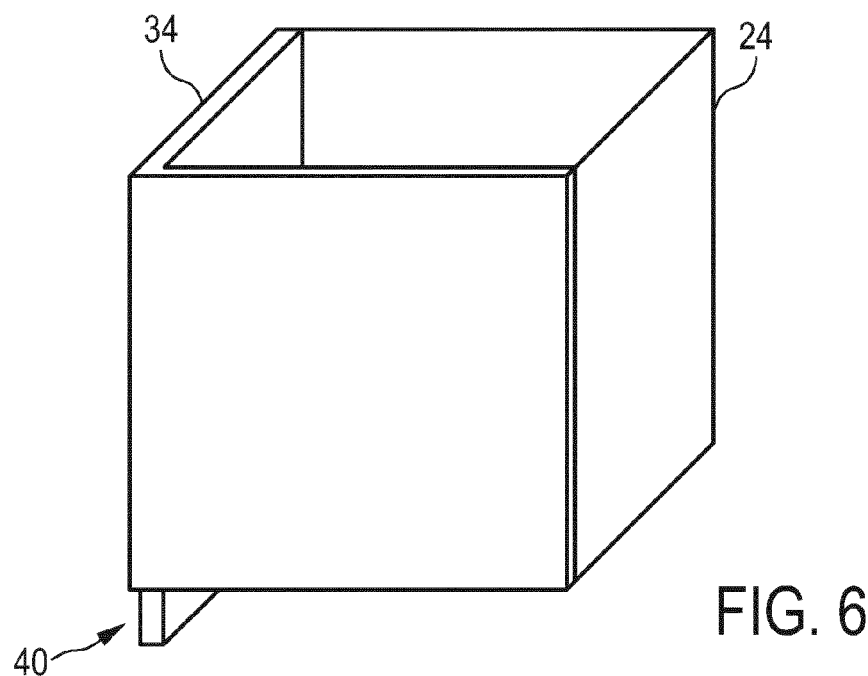
FIG. 6 schematically illustrates a folded flexible substrate.

FIG. 6 shows a flexible substrate 34 for supporting photosensitive elements (printed photodiodes) wrapped or folded around the scintillator element 24. Depending on the used material, the flexible substrate 34 allows achieving a 90° bend and thereby supporting photosensitive elements optically coupled to two surfaces of the scintillator element 24. This may similarly also be extended to all four surfaces of the scintillator 24 orthogonal to the side facing the radiation source. Also, two L-shaped flexible substrates as illustrated in FIG. 6 can be used to cover all four surfaces of the scintillator element. Both possibilities enable complete (or almost complete) 360° coverage and optimized light collection efficiency. Other possibilities such as only partly covering one or more of the surfaces of the scintillator element may be realized analogously.

A further advantage of using a flexible substrate is also illustrated in FIG. 6. For the connection of the flexible substrate 34, it is sufficient that only one overlapping interconnect portion 40 overlaps the scintillator element 24. The flexible substrate 34 may support a plurality of photosensitive elements optically coupled to multiple surfaces of the scintillator element 24. The required connection circuitry can be embedded in the flexible substrate 34, e.g. by means of a printing process. This may reduce the number of connection points to the readout electronics and thereby may result in a more efficient manufacturing or assembly process.

Figure 7:
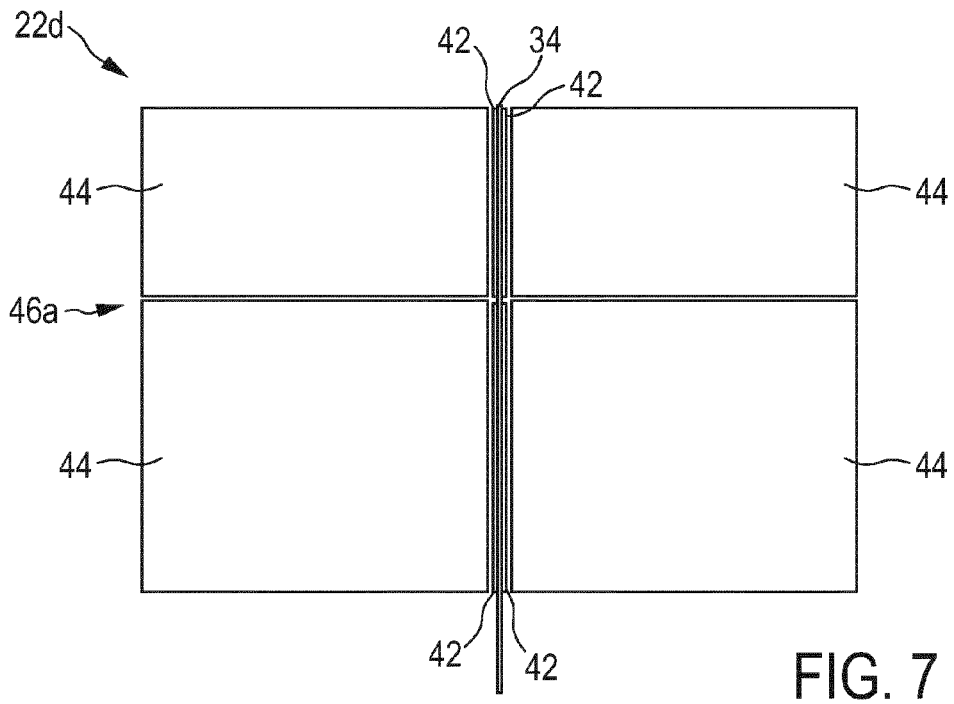
FIG. 7 shows a schematic illustration of a fourth embodiment of a detection module according to the present invention comprising two stacks of scintillator elements and a substrate with photosensitive elements on both sides in side view.

FIG. 7 illustrates yet another embodiment 22d of a detection module according to the present invention in side view. Thereby, the flexible substrate 34 supports four scintillator elements 42 optically coupled to four scintillator elements 44. The photosensitive elements 42 are printed on both sides of the substrate 34. The scintillator elements 44 are arranged in two stacks 46a, 46b of scintillator elements. Such a stack 46a, 46b may particularly allow capturing ionizing radiation of a higher energy bandwidth and/or discriminating the Compton and photo-electric components of the interaction of ionizing radiation with matter. Thus, more information on the energy dependent attenuation properties of tissues can be gained. Usually, the two scintillator elements of one of the stacks 46a, 46b are optically coupled to one another, e.g. glued together by means of light conductive glue. Thus, ionizing radiation may pass through the scintillator element facing the radiation source into the scintillator element initially shielded by the other scintillator element. The emission of scintillation photons can be caused in each of the scintillator elements depending on the energy of the incident radiation. It may also be possible in other embodiments that one stack comprises more than two scintillator elements, that multiple scintillator elements are read out with a single photosensitive element or that one scintillator element is read out by multiple photosensitive elements. It may particularly be advantageous to arrange multiple scintillator elements in a stack, each scintillator element being read out individually by means of a dedicated photosensitive element. In the generated image, an image pixel corresponds to a stack of scintillator elements.

Figure 8:
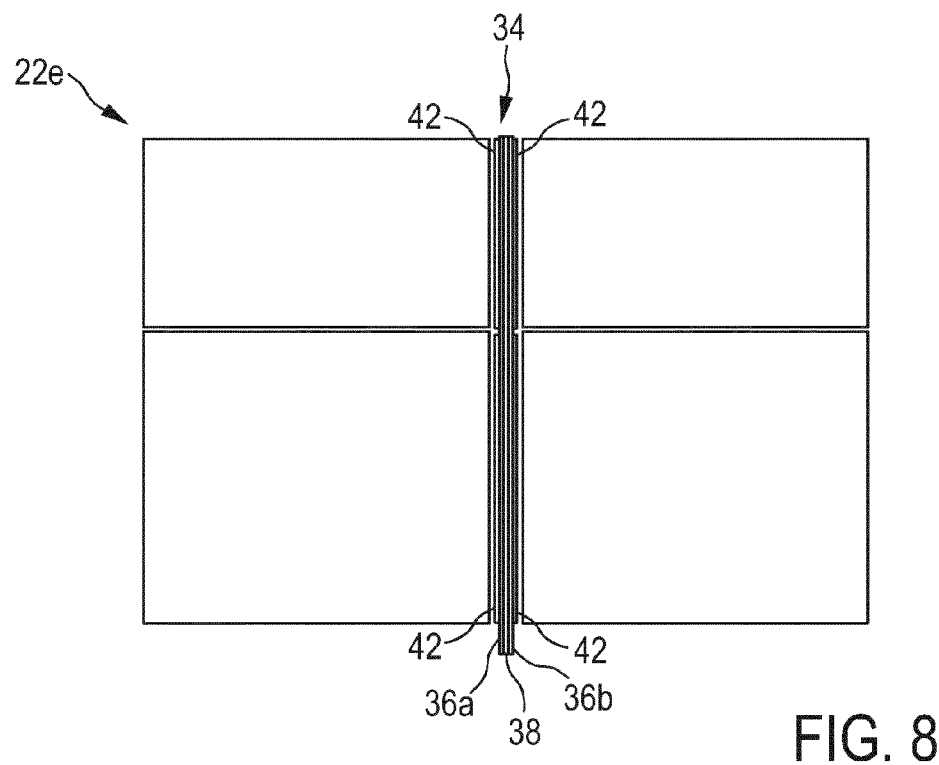
FIG. 8 shows a schematic illustration of a fifth embodiment of a detection module according to the present invention comprising a flexible substrate including multiple layers.

FIG. 8 illustrates another embodiment 22e of a detection module. Thereby, the flexible substrate 34 is composed of two support layers (substrate layers) 36a, 36b, each of which supports photosensitive elements 42 on one of its sides. In between the two support layers 36a, 36b there is arranged an optically intransparent layer 38 in the center of the flexible substrate 34. This optically intransparent layer 38 may be represented by a layer of glue, i.e. optically intransparent glue. Another possibility for the layer 38 is, e.g., a mechanically resilient material may be used to further strengthen the provided mechanical support.

Figure 9:
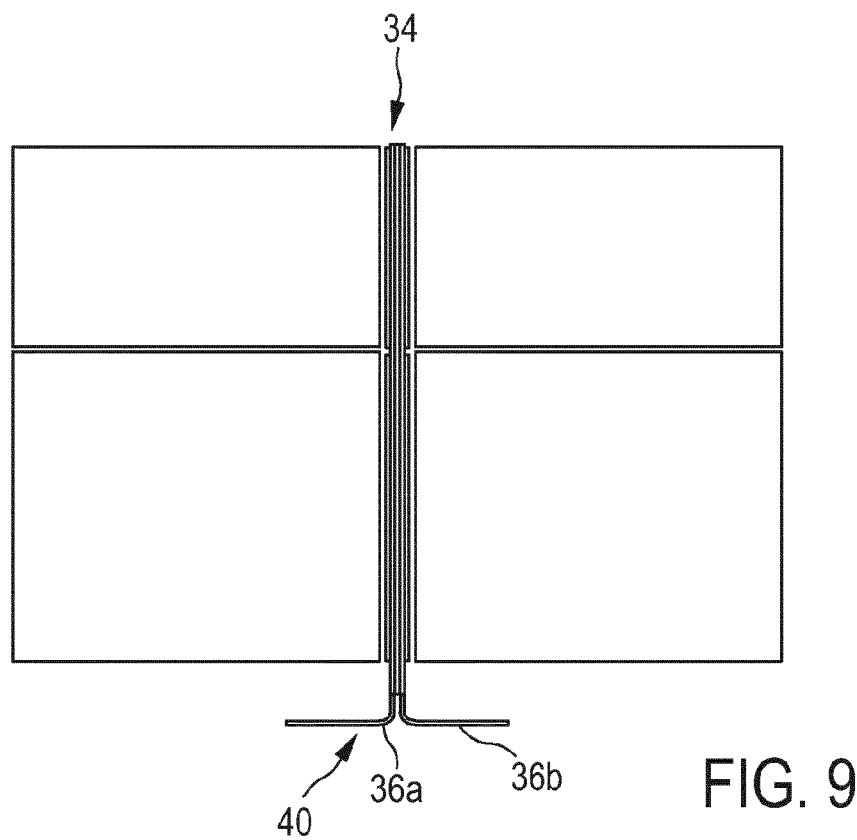
FIG. 9 schematically illustrates a flexible interconnect.

FIG. 9 illustrates one possible approach for interconnecting the flexible substrate 34 as described in FIG. 8 with a readout electronics. Thereby, the flexible substrate 34 and the two support layers 36a, 36b are bent to form an overlapping interconnect portion 40 to allow for easy connection of the detection module with the readout electronics.

Figure 10:
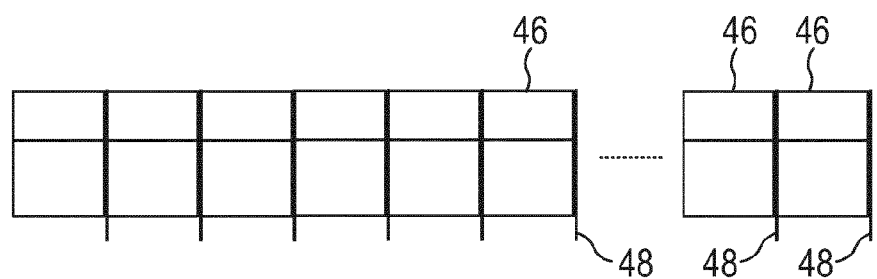
FIGS. 10 and 11 schematically illustrate the advantages resulting from the use of a double-sided flexible substrate in an assembly process.
Figure 11:
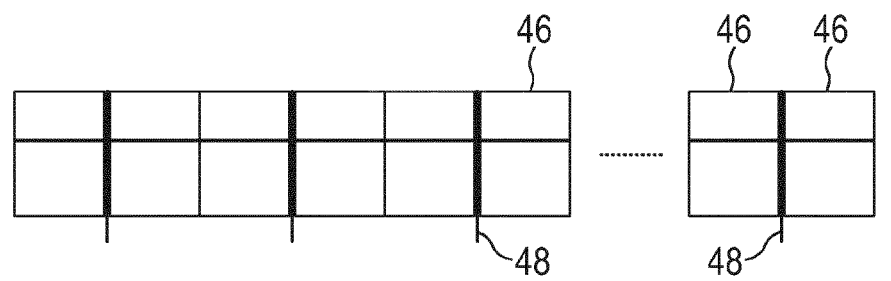

FIG. 10 and FIG. 11 illustrate one advantage in the assembly process that results from the use of a detection module according to the present invention. In FIG. 10, multiple stacks of scintillator elements 46, each with an individual flexible substrate 48, are assembled to form a detection module. In contrast thereto, FIG. 11 shows that the number of scintillator elements 46 that needs to be readout remains the same but the 90° connection to the readout electronics is only necessary in half as many locations. This 90° connection is a main contributor to assembly costs, so there is a lot of potential for cost reduction by reducing the number of assembly points. It may also be possible that fewer interconnection points are required if a flexible substrate supporting photosensitive elements on both of its sides (double-sided photodiode array) is used.

FIG. 12 schematically illustrates a detection module 50 according to another aspect of the present invention. The module 50 comprises a (substantially planar) flexible substrate 34 with two photosensitive elements 52a, 52b on its two surfaces. The module 50 allows the detection of impinging photons 54 (incident radiation) from both sides. In contrast to the above outlined detection of scintillation photons, the module 50 thereby not only allows the detection of scintillation photons but allows the detection of more or less arbitrary radiation 54 depending on the material that is used for the photosensitive elements 52a, 52b. In particular, such a module 50 may be manufactured based on organic electronics, e.g. by means of a printing process in which the photosensitive elements 52a, 52b are sequentially or in parallel printed on both sides of the flexible substrate 34. It may also be possible to glue two or more layers together that support the photosensitive elements 52a, 52b.

The photosensitive elements 52a, 52b can thereby be of different geometries, material, structuring or sensitivity, depending on the application. For instance, it may be possible to print photosensitive elements with different spectral sensitivity on one side or on two sides of a flexible substrate. If the first photosensitive element includes a material suitable for the detection of photons of a first wavelength and the second photosensitive element includes a material suitable for the detection of photons of a second wavelength a two-color (or multi color if more than two photosensitive elements are used) sensitive detector could be obtained at comparably low costs. The photosensitive elements 52a, 52b can be read out by means of photon counting or charge integration.

The flexible substrate can either be transparent for the captured photons or not. Further, it may include multiple layers with different properties, e.g. an intransparent layer. It may also be possible that the flexible substrate 34 is basically integrated with the photosensitive elements 52a, 52b.

The necessary connection circuitry may be included in the flexible substrate 34 or in the photosensitive elements 52a, 52b. It may, however, also be possible that the connection circuitry is partly or entirely integrated by means of an additional printing process or by including conventional devices. Depending on the manufacturing process, it may also be possible to not only print the photosensitive elements but also optical structures such as an optical filter or the like. Naturally, it may also be possible that multiple photosensitive elements are supported on one or two sides of the flexible substrate 34 and also different geometrical structuring of the photosensitive elements on one side or both sides may be possible.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. Detection module for the detection of ionizing radiation emitted by a radiation source comprising:
    a scintillator element for emitting scintillation photons in response to incident ionizing radiation;
    a first photosensitive element optically coupled to the scintillator element for capturing scintillation photons; and
    a flexible substrate for supporting the first photosensitive element;
    wherein the flexible substrate is folded around the scintillator element to cover at least two surfaces of the scintillator element.

2. Detection module as claimed in claim 1, further comprising:
    a second photosensitive element for capturing scintillation photons;
    wherein the flexible substrate is substantially planar; and
    the first photosensitive element is located on a first surface of the substantially planar flexible substrate and the second photosensitive element is located on a second surface of the substantially planar flexible substrate opposite the first surface.

3. Detection module as claimed in claim 2, wherein
    the flexible substrate includes a first support layer for supporting the first photosensitive element and a second support layer for supporting the second photosensitive element; and
    the first and the second support layers are attached to one another by means of glue.

4. Detection module as claimed in claim 2, further comprising a second scintillator element, wherein
    the flexible substrate is arranged in between the first and the second scintillator element; and
    the first photosensitive element is optically coupled to the first scintillator element and the second photosensitive element is optically coupled to the second scintillator element.

5. Detection module as claimed in claim 2, further comprising a second, a third and a fourth scintillator element, wherein
    the first and the third scintillator elements are arranged in a first stack and the second and the fourth scintillator element are arranged in a second stack, one scintillator element in a stack being located in between the radiation source and the other scintillator element in the stack; and
    the flexible substrate is arranged in between the first and the second stack parallel to side surfaces of the first and the second stack.

6. Detection module as claimed in claim 5, further comprising a third and a fourth photosensitive element; wherein
    each of the first, second, third and fourth photosensitive elements is optically coupled to the corresponding first, second, third or fourth scintillator element;
    the third scintillator element is located on the first surface of the substantially planar flexible substrate; and
    the fourth photosensitive element is located on the second surface of the substantially planar flexible substrate.

7. Detection module as claimed in claim 1, wherein the first and/or the second photosensitive element is substantially made of an organic material.

8. Detection module as claimed in claim 1, wherein the flexible substrate is substantially made of an organic material.

9. Detection module as claimed in claim 1, wherein the flexible substrate includes an intransparent layer or is substantially made of an intransparent material for preventing scintillation photons from passing through the flexible substrate.

10. Detection module as claimed in claim 1, wherein the first and/or the second photosensitive element is printed on the flexible substrate.

11. Detection module as claimed in claim 1, wherein
    the scintillator element is substantially cuboid-shaped with a first surface facing the radiation source; and
    the flexible substrate is arranged parallel to a second surface of the scintillator element, said second surface being arranged orthogonal to said first surface.

12. Detection module as claimed in claim 1, further comprising:
    a readout electronics for providing information on the spatial distribution of the incident ionizing radiation;
    wherein the flexible substrate includes a connection circuitry for connecting photosensitive elements to the readout electronics.

13. Imaging device comprising:
    a subject support for supporting a subject in an examination area;
    a radiation source for emitting ionizing radiation arranged on a first side of the examination area or within the subject in the examination area;
    a detection module as claimed in claim 1 arranged on a second side of the examination area for the detection of ionizing radiation emitted by the radiation source; and
    an imaging unit for providing images based on the spatial distribution of the detected ionizing radiation.

14. Detection module for the detection of radiation comprising:
    a first and a second photosensitive element for capturing photons;
    a flexible substrate for supporting the first photosensitive element on a first surface and the second photosensitive element on a second surface;
    wherein the flexible substrate, the first photosensitive element and the second photosensitive element are substantially made of an organic material,
    wherein the flexible substrate is folded around a scintillator element to cover at least two surfaces of the scintillator element.

* * * * *